(12) United States Patent
Heimberger et al.

(10) Patent No.: US 10,478,051 B2
(45) Date of Patent: Nov. 19, 2019

(54) ENDOSCOPIC INSTRUMENT

(71) Applicant: RICHARD WOLF GMBH, Knittlingen (DE)

(72) Inventors: Rudolf Heimberger, Oberderdingen (DE); Sebastian Buccheri, Durmersheim (DE)

(73) Assignee: RICHARD WOLF GMBH, Knittlingen (DE)

( * ) Notice: Subject to any disclaimer, the term of this patent is extended or adjusted under 35 U.S.C. 154(b) by 3 days.

(21) Appl. No.: 15/128,636

(22) PCT Filed: Feb. 19, 2015

(86) PCT No.: PCT/DE2015/200084
§ 371 (c)(1),
(2) Date: Sep. 23, 2016

(87) PCT Pub. No.: WO2015/144146
PCT Pub. Date: Oct. 1, 2015

(65) Prior Publication Data
US 2017/0105604 A1  Apr. 20, 2017

(30) Foreign Application Priority Data

Mar. 25, 2014 (DE) .................. 10 2014 205 556

(51) Int. Cl.
*A61B 1/005* (2006.01)

(52) U.S. Cl.
CPC .......... *A61B 1/0055* (2013.01); *A61B 1/0057* (2013.01)

(58) Field of Classification Search
CPC ............... A61B 1/0055; A61B 1/0057; A61M 25/0051; A61M 25/0138; A61M 39/1055
USPC ....................................... 604/95.01
See application file for complete search history.

(56) References Cited

U.S. PATENT DOCUMENTS

2006/0111615 A1* 5/2006 Danitz ............... A61B 1/00071
  600/141
2013/0226151 A1* 8/2013 Suehara ............ A61M 39/1055
  604/533

FOREIGN PATENT DOCUMENTS

DE    10 2005 054057 A1    6/2007
JP    2008 099827 A         5/2008
JP    2011 152361 A         8/2011

* cited by examiner

*Primary Examiner* — Phillip A Gray
(74) *Attorney, Agent, or Firm* — McGlew and Tuttle, P.C.

(57) ABSTRACT

An endoscopic instrument with a shank which includes at least two segments which are connected to one another via diametrically opposite joints. Between axial face edges of the opposite joints facing one another a gap is present. The gap runs with at least one angular bend.

18 Claims, 2 Drawing Sheets

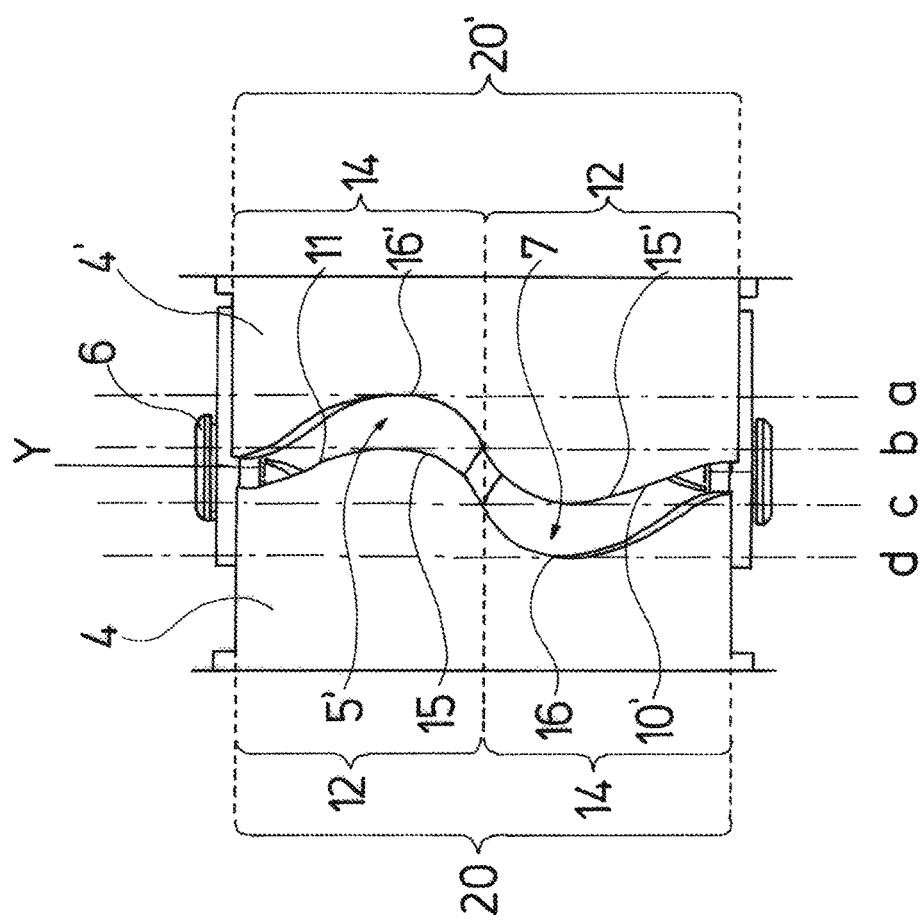
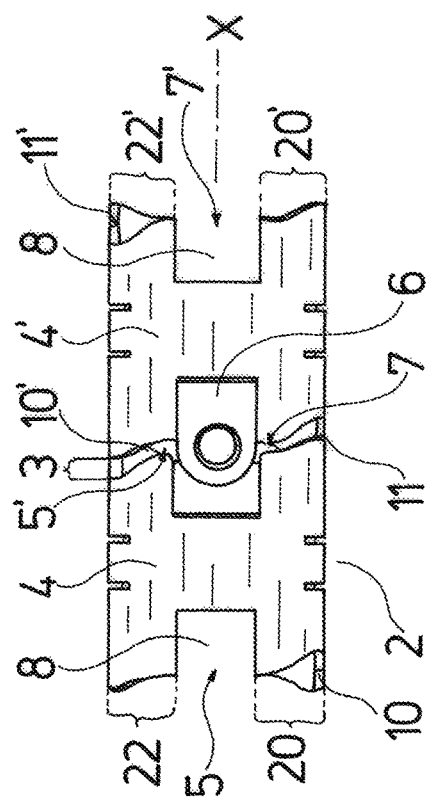
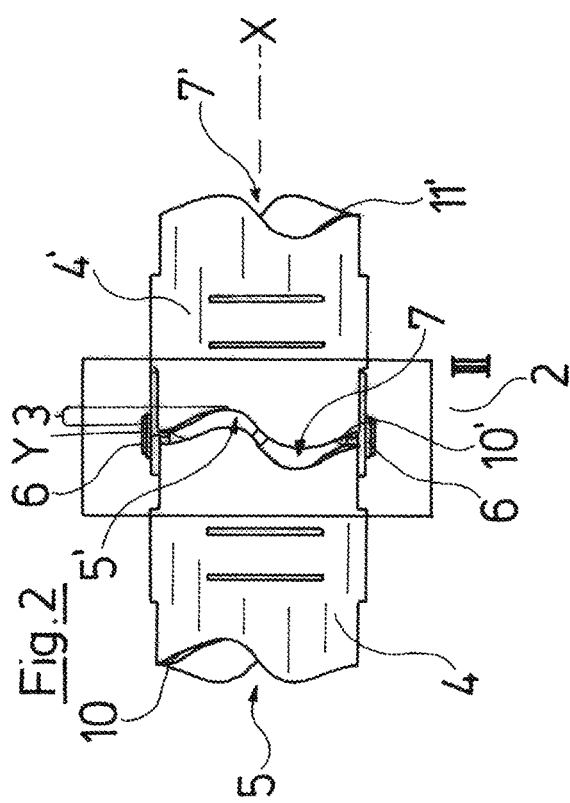

ENDOSCOPIC INSTRUMENT

CROSS REFERENCE TO RELATED APPLICATIONS

This application is a United States National Phase Application of International Application PCT/DE2015/200084 filed Feb. 19, 2015, and claims the benefit of priority under 35 U.S.C. § 119 of German Application 10 2014 205 556.3 filed Mar. 25, 2014, the entire contents of which are incorporated herein by reference.

FIELD OF THE INVENTION

The invention relates to an endoscopic instrument with a shank.

BACKGROUND OF THE INVENTION

Endoscopic instruments with a flexible shank, with which an actively controllable section of the shank consists of several segments manufactured from tube sections, are already known. These segments are connected to one another in a pivotally movable manner by way of joints. Tension or pull means which are led in the inside of the segments, serve for the control of the pivot movement. For the pivot movement, it is necessary for an adequately large gap to be present between two adjacent segments, so that the pivoting movement is not limited to small angles due to mutual contacting of the segments. The actively controllable section of the shank is coated with a flexible tube which seals the components installed in the instrument, to the outside, and represents a barrier to the surroundings.

Thereby, a common problem is thereby the fact that folds or creases occur in the flexible tube, and these are caused over the course of time when using the endoscopic instrument. Thus inwardly arched folds can occur between two adjacent segments in the region of the gaps. The flexible tube can thereby become clamped between the segments. This can lead to a restriction of the pivot movability of the flexible shank as well as to a perforation of the flexible tube. Approaches for solving this problem lie in the provision of additional fine meshwork between the flexible section and the flexible tube, as well as the use of a thick-walled flexible tube which is less prone to the formation of creases or folds. Likewise, it is known to apply many short segments, so that the complete angled bending of the endoscopic instrument is achieved by only small pivot movements of the segments, and the gaps between two adjacent segments can therefore be kept small. The disadvantage of such solution is the fact that an additional meshwork as well as a thick-walled flexible tube leads to an increased outer diameter of the endoscopic instrument, whereas short segments increase the assembly effort and enlarge the bending radius.

SUMMARY OF THE INVENTION

Against this background, it is the object of the invention, to provide an endoscopic instrument with a shank, with which the clamping of an outer flexible tube between two segments of a section of a shank can be prevented in a simple manner.

The endoscopic instrument according to the invention, with a flexible shank or a flexible shank section comprises at least two segments which are connected to one another via two diametrically opposed joints. The shank either as a whole can be designed in a flexible manner from several segments which are connected to one another via joints, or however can comprise at least one flexible section, in which at least two segments are connected to one another via joints. The joints are thereby arranged at the ends of the segments which are axial with respect to the longitudinal axis of the shank, and connect adjacent segments to one another in a pivotably movable manner. The joints are arranged on the segments in a diametrically opposed manner such that they have a common rotation axis. The face edges of the segments are divided by the joints in each case into two regions, wherein a region is delimited at its ends in each case by two joints, and wherein both regions of a face edge of a segment are preferably equally long in the peripheral direction of the segment. The joints therefore with respect to the middle point of a peripheral line of the segment are preferably arranged on the face edge in an exactly opposite manner. The face edges of the two connected segments which axially face one another, between themselves comprise a gap, wherein according to the invention, the gap runs in an angled manner at least once.

According to the invention therefore, the gap in at least a part-piece runs angled to the peripheral direction at least once, which is to say this part-piece extends at an angle to the cross-sectional plane of the shank which is normal to the longitudinal axis. The two segments, between whose axial face edges facing one another the gap is arranged, are therefore preferably designed such that a plane which is parallel to the rotation axis of the joints connecting the segments cannot intersect the gap without simultaneously contacting or intersecting at least one of the axial face edges of the segments.

Folds or creases mostly form in the part of a flexible tube surrounding the flexible shank, said part being situated close to the joints. These folds mostly run along the intersection lines of the flexible tube with the planes, in which the rotation axis of the two joints lies. If the gap now runs as envisaged according to the invention, then the penetration of the folds into the gap is prevented, since the gap thus also extends in a manner angled to the forming folds. All deformations and in particular all deformations directed in the direction of the endoscopic instrument, in the flexible tube can likewise be considered as folds in the context of the invention.

The gap preferably has a constant width along its extension, preferably in the axial direction of the shank. The width of the gap is the extension of the gap between two oppositely lying axial face edges perpendicularly to the rotation axis of the two joints connecting the adjacent segments. The width of the gap is thereby not constant in the strict sense. The distance to the face edges which face one another and thus also the width of the gap changes in a manner depending on the angle due to the angled bending of two adjacent segments. Constant is understood as being given when the width of the gap between the two axial face edges along the extension of the face edges of the segments has an essentially constant width in the non-angled position of the segments.

The axial face edges of the segments which face one another preferably at least in a part-region between the joints run curved parallel to the axis at least once and/or comprise at least one sharp bend. The axially parallel course of an axial face edge is to be understood in that it extends within or along a peripheral surface which runs parallel to the longitudinal axis of the shank or of the segments. The axial face edge thereby at least partly does not run in the peripheral direction to the longitudinal axis, but, as described, in a manner angled at least once, for forming the angled gap.

As described above, one succeeds in the axial face edges of the segments not running completely in a plane parallel to the rotation axis of the joints, by way of the course of the axial face edges which face one another, said course being curved at least once or angularly bent, parallel to the axis. The engagement of the flexible tube into the gap between the segments is therefore prevented.

An axial face edge is also to be understood as an axial end-face of the peripheral wall of the segments, on account of the possible material thickness and material shape of the segments at their axial ends.

According to a preferred embodiment of the invention, the axial face edges of the two segments which face one another, between the two joints run in such a wave-like or angled manner that each axial face edge comprises at least one first section which projects axially further with respect to at least one adjacent second section. The first section e.g. in the direction of the longitudinal axis of the shank thus lies further distally than the adjacent second section of the same face edge. The shaping of the adjacent face edges with first and second sections advantageously does not permit the gap between two axial face edges facing one another to run peripherally to the longitudinal axis in a continuous manner, but in a waved or angled manner. This prevents the penetration of long folds of the flexible tube into the gap between the segments.

The axial face edges of two segments which face one another are divided by the diametrically oppositely arranged joints, in each case in two regions, and both regions preferably each comprise at least one first section and a second section, of which the first section projects further axially compared to the second section. Each region corresponds to a part of the face edge which extends along the outer wall of the segment between the two adjacent joints. Together, both regions form the complete extension of the axial face edge at an axial end of a segment.

The first section of an axial face edge of a first segment preferably lies opposite a second section of the facing, axial face edge of an adjacent segment. Thus, a width of the gap which is essentially constant above all in the axial direction, without the gap extending continuously in the peripheral direction of the contacting segments, can therefore preferably be implemented in the case of a suitable shaping of the first and second sections. The axial face edges of adjacent segments which face one another preferably run in a complementary manner. Thus a first section of the one axial face edge can project into the free space in front of the second axial section of the facing other axial face edge, and on pivoting can move in the free space within a certain angular region without contacting the adjacent segment.

As described above, the joints divide each face edge into two regions. The opposite lying regions of axial face edges of two adjacent segments, said face edges facing one another, are preferably likewise shaped complementarily to one another. Thus, directly opposite a first section of one region is a second section of the oppositely region, and vice versa. As described above, the gap between two regions thus preferably has a constant width along the extension of the regions. Particularly preferably, the four regions of two opposite face edges (two regions on each face edge) are shaped such that the gap formed between them has a constant or almost constant width peripherally of the longitudinal axis. This prevents the penetration of the flexible tube into the gap and simultaneously permits a desired angular bending ability. Moreover, all four regions are advantageously either shaped identically or complementarily to one another, wherein in each case two regions are preferably shaped complementarily to one another and one of the two remaining regions shaped identically to each of these two regions. Thus for example identical segments can lie opposite one another in a manner rotated by 180° to one another.

With a preferred embodiment of the invention, the axial face edges of two adjacent segments which face one another are curved in an axially parallel S-shaped manner and/or comprise tooth-like (comb-like or undulating) structures parallel to the axis. An axial face end which is curved in an S-shaped manner parallel to the axis is to be understood in that one of the regions and preferably both regions of the axial face edge in each case comprises at least one first section and a second section adjacent to one another, wherein the sections are shaped such that the respective region in a peripheral surface runs curved in an S-shaped manner about the longitudinal axis of the shank. Embodiments which are merely similar or complementary to an S-shape which is to be recognized in profile are thereby also included. Moreover, a region can be shaped by further alternating first and second sections according to the preceding description and extend along the peripheral surface in a wave-like manner. The axis-parallel tooth-like structures are to be understood in that first sections and second sections on at least a region of an axial face edge run in a peripheral surface about the longitudinal axis similarly to an undulating or comb-like structure, in the form of several prong-like projections with intermediate free spaces. The axial end with the described regions of the axial face edge thus comprises axially directed projections which are similar to the prongs of a comb. Opposite, axial face edges of two adjacent segments are preferably shaped such that a prong on one axial face edge engages between two prongs of the opposite axial face edge and vice versa.

The mentioned tooth-like structures for example are advantageous if the material of the flexible tube tends to a fold formation with short folds. With the prong-like projections of the tooth-like structure, it is possible to form the gap in a very small manner in the peripheral direction between the prongs of two adjacent segments close to the joints, without thereby compromising the movability, in particular the angled bending ability. A penetration of the flexible tube can thus be prevented. The prongs with regard to their shape and number can be designed such that the axial face edges of adjacent segments which face one another only comprise extremely short part-regions which run peripherally to the longitudinal axis in a continuous manner. The prongs can likewise engage into the adjacent segment into corresponding free spaces, for example between two prongs, to sufficiently far extent, so that they support the flexible tube on the inner periphery over a larger axial length.

As described, it is advantageous if preferably the contours of the axial face edges of two adjacent segments, said face edges facing one another, at least partly engage into one another. As already specified, free spaces result at the axial ends of each segment due to the shaping of the face edges with first and second sections, in comparison to a peripherally running axial face edge. The axial face edges of two adjacent segments are shaped such that they mutually engage into the free spaces of the opposite axial ends, so that a gap between the segments, in the direction parallel to the rotation axis of the adjacent joints only comprises small part-regions which run peripherally to the longitudinal axis of the shank. The penetration even of small folds of the flexible tube into the gap is therefore prevented.

According to a preferred further development of the invention, two adjacent segments in their axis-parallel alignment are axially distanced to one another in a manner such that the plane perpendicular to the axis and on the apex of at least one first section of the first segment, touches or preferably intersects at least a first section of the adjacent second segment which lies closely adjacent the first section of the first segment. In the case of an alignment which is parallel to the axis, i.e. of a straight alignment of two adjacent segments along the longitudinal axis of the shank, the longitudinal axes of both segments are aligned to one another. The segments are therefore not angled to one another. The axis-perpendicular plane on the apex at least of a first section corresponds to a plane which parallel to a peripheral line of the segment contacts the first section at the point, which is distanced furthest to the axial middle of the segment, i.e. projects furthest axially. The apex of a first section of an axial face edge therefore in the axial direction is preferably distanced further to an apex of a second adjacent section of the same axial face edge than the apex of a first section of an opposite segment which is opposite the mentioned second section.

With a further preferred embodiment, at least part-pieces of the axial face edges of two segments which are opposite which is to say are adjacent one another, are in contact with one another given a position of these segments, in which these segments are maximally angled to one another. At least one contact point or region, at which the adjacent segments contact one another therefore results. This can effect the limitation of the pivot movement of the flexible shank or a flexible section of the shank. Likewise, the mutual contact of the adjacent segments at several locations gives the shank stability with respect to mechanical forces which otherwise act only upon the joints and/or existing pull means as contact points between the segments.

With a condition of adjacent segments angled to one another, the gap in its width parallel to the longitudinal axis is no longer constant or almost constant everywhere along its extension. Two regions of the two opposite axial face edges which face one another, in an angled position are distanced further to one another than in the non-angled condition of the segments. The gap between these regions is widened in comparison to the non-angled condition. The opposite face edges in this region are preferably shaped such that, as described, they comprise first and second sections which still engage into one another also in this pivoted-apart position, so that a continuous gap continues is still not formed in the peripheral direction. The other two, diametrically opposite regions facing one another in contrast are closer to one another in the angularly bent or angled position. The gap between these two regions is reduced in size at least in its width. The face edges which face one another, as described above, are preferably shaped with first sections and second sections such that on the one hand they prevent the penetration of the flexible tube into the gap at each angled position, and on the other hand that the angled bending is not restricted in the angular region, for which the endoscopic instrument is envisaged.

Moreover, it is advantageous if preferably at least two segments are shaped identically. Identically shaped segments can thus be applied at different locations of the flexible shank. Particularly preferably, several or all segments are equally shaped. This reduces the part variety and reduces the costs.

According to a preferred embodiment of the invention, an instrument head is joined on an end of the distal segment of the shank. The instrument head forms the distal instrument end with the windows and openings for optical systems, rinsing channels and instruments. The instrument head thereby, as an autonomous component, can be arranged on the flexible shank or on the flexible section or be integrally formed as one piece on the end of a segment.

Moreover, it is preferable for pull means to be led through at least parts of the segments. These pull means for example can be connected to the instrument head and/or to other subsequent segments and permit a control of the deflection of the flexible shank or flexible section of the shank. Guides can be formed in the segments for the pull means.

With a particular embodiment, the pull means are connected to at least one of the segments. By way of this, there is the possibility of controlling the angular bending of this at least one segment by way of a force being exerted onto the segment via the pull means.

The pull means are preferably arranged such that the axial face edges cannot contact the pull means on angularly bending two adjacent segments. This can prevent a clamping of the pull means and thus a hindering of the controllability of the deflection.

According to a further advantageous embodiment, the segments and at least parts of the joints are designed as one piece. Thus, the joint or a joint part can be manufactured as one piece together with the segment from one work-piece, so that no further assembly of the joint parts or joints for fastening on the segment is necessary.

A preferred embodiment envisages the flexible shank or the flexible section of the shank being encased at least in sections with a flexible tube. This flexible tube which is attached on the endoscopic instrument can form the outer envelope (sheath) of the complete shank. The flexible tube however can also be arranged only on a section of the shank. In particular, it can thereby be arranged at the outer periphery on the flexible section with the at least two segments. The flexible tube for example serves for the protection of the flexible shank with respect to the penetration of foreign bodies. At the same time, it prevents tissue from being injured by the flexible shank. This flexible tube is prevented from penetrating into gaps between the axial face edges of the segments of the shank due to the previous described design of the segments.

The invention is hereinafter explained in more detail by way of an embodiment example represented in the drawing. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which an embodiment of the invention is illustrated.

BRIEF DESCRIPTION OF THE DRAWINGS

In the drawings:

FIG. 1 is a lateral view of two segments of a flexible section of a shank in the non-angled position;

FIG. 2 is a lateral view of the two segments according to FIG. 1;

FIG. 3 is an enlarged representation of the detail III in FIG. 2;

DESCRIPTION OF THE PREFERRED EMBODIMENT

Figure 4:
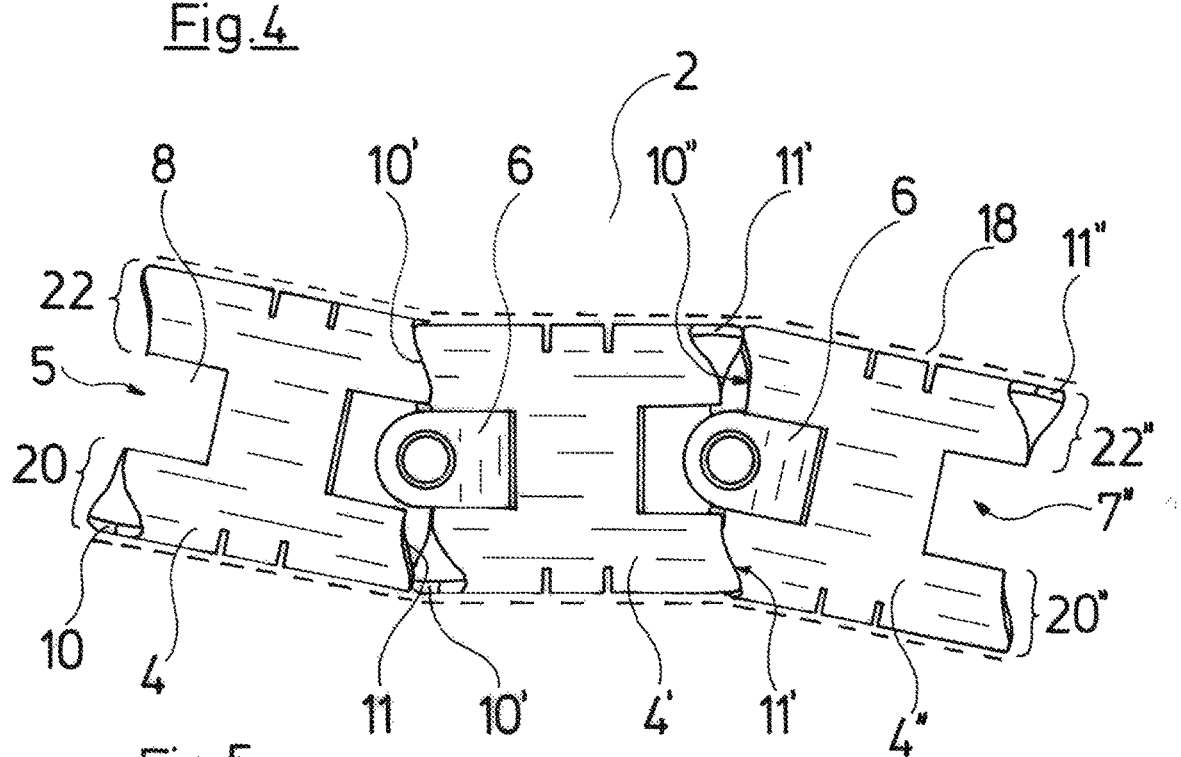
FIG. 4 is a lateral view of three segments of the flexible section of the shank in an angled position.

Referring to the drawings, in the shown embodiment example, two segments 4, 4' of a flexible shank or of a flexible section of a shank 2 of an endoscopic instrument are shown. The two segments 4, 4' are shaped in an identical manner and with regard to their basic shape form a hollow cylinder. The non-angled position of the segments 4, 4' to one another and which is shown in FIGS. 1 to 3 is defined in that both segments 4, 4' are aligned along the longitudinal axis X of the shank 2, and the segments 4, 4' are aligned with one another. Each segment 4, 4' at its first axial end 5, 5' and its second axial end 7, 7' in each case comprises an axial face edge 10, 11, 10' 11'. Two adjacent segments 4, 4' at their facing axial ends 7, 5' are connected to one another in a pivotably moveable manner by way of two joints 6 which are designed as rotation joints. The two joints 6 are thereby mounted in recesses 8, in each case on the outer side of the segments 4, 4', lie on the first axial end 7 of the segment 4 and on the second axial end 5' of the segment 4' in a diametrically opposed manner and thus have a common rotation axis Y (FIG. 2). The joints at the face edges 10, 11' (or 10, 11" in the FIGS. 4 and 5) are not drawn in the figures. Parts of the joints 6 can also be manufactured as one piece with the segment 4, 4', instead of recessing the complete joints 6 into the recess 8. This simplifies the assembly since the parts of the joints 6 can be formed from the same work-piece as the segments 4, 4'.

The two joints 6 or recesses 8 in each case divide the adjacent axial face edges 10, 11, 10', 11' into a first region 20, 20' and into a second region 22, 22'. The axial face edge 11 on the second axial end 7 of the first segment 4 faces the axial face edge 10' at the first axial end 5' of the adjacent second segment 4'. A gap 3 is located between the axial face edges 11, 10' of the adjacent segments 4, 4' which face one another. The axial face edge 10 and 10' is shaped complementarily or almost complementarily to the axial face edge 11 and 11' respectively. Each axial face edge 10, 10', 11, 11' along an axial face edge extension comprises first sections 12 and second sections 14 lying next to one another, wherein a first section 12 projects further in the axial direction than at least one adjacent second section 14 of the same axial face edge 10, 10', 11, 11'. Given axial face edges 11 and 10' of adjacent segments 4 and 4' which face one another, a first section 12 always lies opposite a second section 14 and vice versa, according to the at least approximately complementary shaping of the axial face edge 10, 11 and 10', 11' on a segment 4 and 4' respectively.

The axial face edges 10, 11, 10', 11' of the segments 4, 4' within a peripheral surface which is parallel to the longitudinal axis X have an S-shaped or curved shape. The curved shape consists of the first sections 12 and second sections 14, wherein a second section 14 (FIG. 3) along the axial face edge 10, 11, 10', 11' connects to each first section 12 and vice versa. The transition from one section to the other is therefore effected in a continuous (gradual) manner, so that a wave-like contour is formed. A first region 20' of the axial face edge 10 ' which belongs to the segment 4' and which faces the axial face edge 11 of the segment 4, in its shape and beginning at one of the two joints 6 comprises a second section 14, subsequent to which a first section 12 follows, and this first sections ends at the second joint 6 (FIG. 3). The second region 22' of the axial face edge 10' (cannot be recognized in FIG. 3) is shaped inversely to the first region 20'. The region 22' on the first joint 6 thus at the beginning comprises a first section 12, whereupon a second section 14 ending at the second joint 6 follows. The second region 22 of the axial face edge 11 and the second region 22' of the axial face edge 10' are shaped at least approximately inversely or complementarily to one another. The first region 20 of the axial face edge 11 is shaped at least approximately inversely or complementarily to the first region 20' of the axial face edge 10'. Moreover, thereby the first region 20 of the axial face edge 11 is preferably shaped at least approximately identically to the second region 22' of the axial face edge 10'. Likewise the second region 22 of the axial face edge 11 and the first region 20 of the axial face edge 10' have a shaping which is at least almost identical to one another. Thus, preferably at least almost inversely or complementarily shaped regions 20, 20' and 22, 22' are opposite one another at two opposite axial face edges 10, 11', wherein diametrically opposed regions 20, 22' and 22, 20' are shaped in an almost identical manner.

Thus both regions 20, 20', 22, 22' of an axial face edge 10, 11, 10', 11' are shaped in a wave-like manner along the peripheral surface which is parallel to the longitudinal axis X. The apex 15, 15' of each first section 12 of a face edge 10, 11, 10', 11' is the point of this first section 12 which projects axially to the greatest extent. The apex point 16, 16' of a second section 14 of a face edge 10, 11, 10', 11' is the point of this second section 14 which lies axially inwards to the greatest extent (the point which is situated closest to the axial middle of the segment). The apex 15 of each first section 12 of the axial face edge 11 of a segment 4 in the axial direction X is situated closer to the opposite apex 16' of the adjacent segment 4' than at least an apex 15' of the same axial face edge 10' which is adjacent the apex 16'. A tangent a to the apex 16' of a second section 14 on the axial face edge 10' of the segment 4' is distanced to a tangent b to an apex 15 of the first section 12 of the axial face edge 11 of the segment 4 and opposite the apex 16', axially to a lesser extent or equally far, than tangent c contacting the apex 15' of a first section 12 of the axial face edge 10' of the segment 4' and adjacent the apex 16', is to the tangent a, or is equally distanced to this. Likewise, with regard to the tangent d to the apex 16 of a second section 14 of the axial face edge 11 of a segment 4, said apex lying opposite the apex 15' and being adjacent the apex 15, it is the case that the axial distance of the tangent d to the tangent c is smaller or equal to the axial distance of the tangent d to the tangent b.

The gap 3 between the axial face edges 11, 10' facing one another, has a width which at least does not fall sort of a certain value given a flush alignment of the segments 4, 4' to one another along the longitudinal axis X. This value results from the pivotability of the two segments 4 and 4' to one another, which is to be achieved. With an alignment of the segments 4, 4' which is not angled to one another, the gap 3 at least along the extension of the axial face edges 11, 10' has an essentially constant width in the direction of the longitudinal axis X. The width of the gap 3 in the case of a complementarily shaping of the axial face-edges 11, 10' which face one another results for example on account of the axial distance of the tangents d to c or b to a.

A first section 12 of the segment 4 always lies opposite a second section 14 of the segment 4' and vice versa, due to the at least almost complementary shaping of the axial face edges 11, 10' of the segments 4, 4' which face one another. This ensures the pivoting ability of the shank 2 or the flexible section of the shank 2, since the section 12 projecting axially further, engages into the axially retracted section 14. The first regions 20, 20' and second regions 22, 22' of an axial face edge 10, 11, 10', 11' run similarly to an inversely extended S and extended S respectively, along the peripheral surface running to the longitudinal axis X.

Figure 5:
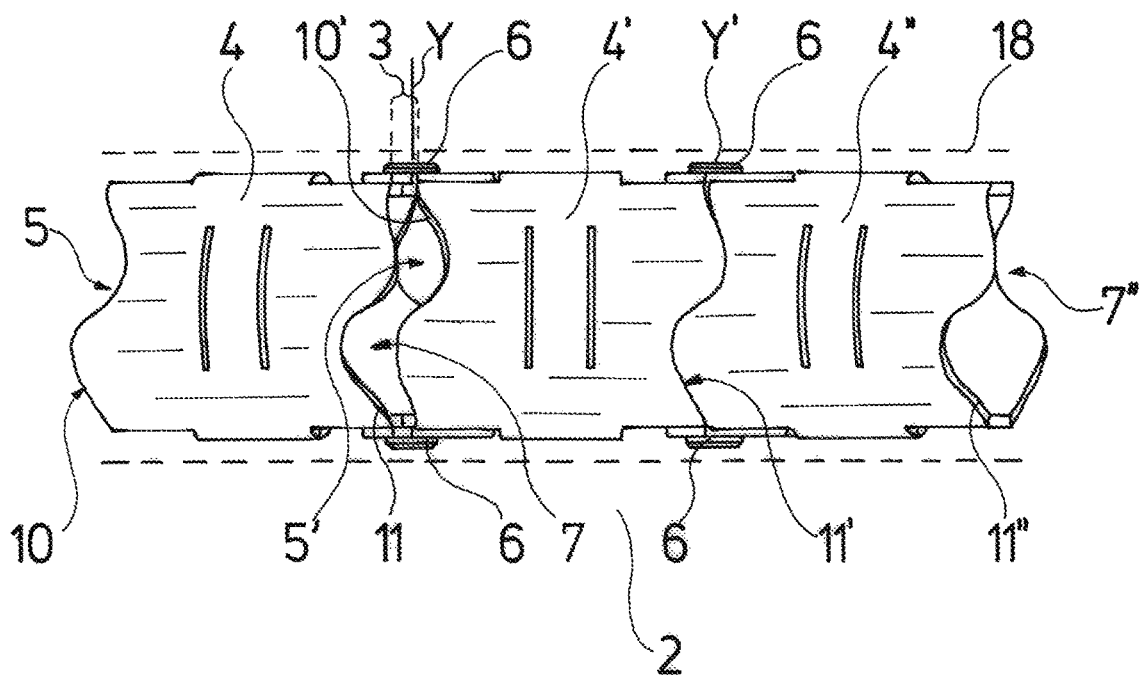
FIG. 5 is a lateral view of the flexible section according to FIG. 4, seen from the lower side in FIG. 4.

With the example of three segments 4, 4', 4", in FIGS. 4 and 5 one can recognize that a segment 4 and 4' can be angled with respect to an adjacent segment 4' and 4" respectively, in an anticlockwise as well as clockwise manner with respect to the rotations axes Y, Y' resulting due to the joints 6, 6'. FIG. 5 shows how the segment 4 is angled in a clockwise manner with respect to the segment 4' on the common rotation axis Y, whereas the segment 4' itself is angularly bent in an anticlockwise manner with respect to the segment 4'. In the maximally angled position of two adjacent segments 4, 4' and 4', 4", in each case at least parts of first sections 12 of the segments 4 and 4' respectively engage past at least parts of the second sections 14 into the adjacent segment 4' and 4" respectively and vice versa, and the parts of the axial face edges 11, 10' and 11', 10" of the adjacent segments 4, 4' and 4', 4" respectively, bear on one another and contact at least at locations. The contacting axial face edges 11, 10' and 11', 10" thus delimit the angled bending of the segments 4, 4' and 4', 4" respectively, to one another. One can recognize from the example of the angled bending of the segment 4 with respect to the segment 4' (FIGS. 4 and 5), that given a maximal clockwise angular bending on the rotation axis Y, parts of the second region 22' of the axial face edge 10' and parts of the second region 22 of the axial face edge 11 contact one another. The contacting of the two regions can also run along their complete extension. A gap 3 would therefore no longer be present between the two regions 22' and 22 of the axial face edge 11. The gap 3 between the first region 20' of the axial face edge 10' and the first region 20 of the axial face edge 11 has widened with the exemplary angled bending.

The first sections 12 and second sections 14 of the two first regions 20' and 20 which lie opposite one another are designed in such an S-shaped or wave-like manner, that the gap 3 between the oppositely lying first regions 20' and 20 with their maximal spacing continues to run in an angled manner at least once. The distance between the tangent b of an apex 15 of the first region 20 and a tangent a to the apex 16' of the first region 20' which lies opposite the apex 15 is smaller or equal to the distance between the tangent a to the mentioned apex 16' and the tangent c to an apex 15' of the first region 20', wherein the apex 15' and the apex 16' lie adjacent one another. Likewise, the distance between the tangent d to the apex 16 of the first region 20 and the tangent c to the apex 15' opposite the apex 16 is smaller or equal to the distance between the tangent d and tangent b, wherein the tangent b contacts an apex 15 which is adjacent the apex 16.

A flexible tube 18 which seals the mechanics in the inside of the shank 2, to the outside, peripherally surrounds the segments 4, 4', 4" of a flexible shank 2. The flexible tube 18 represents a barrier between the outer environment and the components which are located in the shank 2, such as pull means for example, which prevents the penetration of tissue of fluid into the inside of the instrument. A recycling of the instrument is possible since only the outer side of the shank and the flexible tube get into contact with foreign matter.

The axial face edges 10, 11, 10', 11' 10", 11" preferably comprise first sections 12 and second sections 14, corresponding to the preceding description, such that a penetration of the flexible tube 18 into a gap 3 along the extension of the axial face edges 10, 11, 10', 11', 10", 11" is prevented.

While specific embodiments of the invention have been shown and described in detail to illustrate the application of the principles of the invention, it will be understood that the invention may be embodied otherwise without departing from such principles.

The invention claimed is:

1. An endoscopic instrument with a flexible shank, the flexible shank comprising:

two diametrically opposed joints; and at least two segments connected to one another via the two diametrically opposed joints, wherein between axial face edges of the least two segments, which axial face edges are facing one another, a gap is present, wherein the gap runs in an angled manner at least once, wherein a width of the gap is constant along an entire extension of the gap in a non-angled position of the at least two segments, wherein the axial face edges of the segments which face one another, at least in a part region between the joints, run in a curved manner parallel to the axis at least once and/or comprise at least one angular bending, one of the axial face edges extending continuously from an area adjacent to one of the joints to an area adjacent to another one of the joints, another one of the axial face edges extending continuously from another area adjacent to the one of the joints to another area adjacent to the another one of the joints, wherein the one of the axial face edges is located at a constant distance from the another one of the axial face edges.

2. An endoscopic instrument according to claim 1, wherein the axial face edges of the two segments which face one another, between the two joints run in a wave-like or angled manner, such that each face edge comprises at least one first section which projects axially further compared to an adjacent second section.

3. An endoscopic instrument according to claim 1, wherein the axial face edges of two segments which face one another are divided by the diametrically oppositely arranged joints into two regions, and both regions comprise at least a first section and a second section, of which the first section projects further axially compared to the second section.

4. An endoscopic instrument according to claim 2, wherein the first section of the axial face edge of a first segment lies opposite the second section of the opposite axial face edge of the adjacent segment.

5. An endoscopic instrument according to claim 1, wherein the axial face edges of two adjacent segments, which face one another, comprise engagements curved in an S-shape, parallel to the axis and/or tooth engagements parallel to the axis.

6. An endoscopic instrument according to claim 1, wherein the contours of the axial face edges of two adjacent segments, said face edges facing one another, at least partly engage into one another.

7. An endoscopic instrument according to claim 1, wherein two adjacent segments in axis-parallel alignment are axially distanced to one another, whereby a plane perpendicular to the axis and on an apex of at least a first section of the first segment contacts or preferably intersects at least a first section of the facing second segment which lies closely adjacent the first section of the first segment.

8. An endoscopic instrument according to claim 1, wherein in a condition of being maximally angled to one another, at least part-regions of the axial face edges of two adjacent segments, said face edges facing one another, are in contact with one another.

9. An endoscopic instrument according to claim 1, wherein at least two segments are identically shaped.

10. An endoscopic instrument according to claim 1, further comprising an instrument head integrated at one end of a segment.

11. An endoscopic instrument according to claim 1, wherein pull means are led through at least parts of the segments.

12. An endoscopic instrument according to claim 10, wherein the pull means are connected to at least one of the segment.

13. An endoscopic instrument according to claim 1, wherein the segments and at least parts of the joints are designed as one piece.

14. An endoscopic instrument according to claim 1, wherein the shank is surrounded by a flexible tube, at least in sections.

15. An endoscopic instrument according to claim 1, wherein each of the axial face edges comprises a first apex portion and a second apex portion, the first apex portion defining a greatest axial extent of a respective one of the least two segments, the second apex portion being located axially inward of the first apex portion with respect to a longitudinal axis of the respective one of the at least two segments, the first apex portion of one of the at least two segments being located axially opposite the second apex portion of another one of the at least two segments, the second apex portion of the one of the at least two segments being located axially opposite the first apex portion of the another one of the at least two segments, wherein a first axial distance is defined between the first apex portion of the one of the at least two segments and the second apex portion of the another one of the at least two segments and a second axial distance is defined between the first apex portion of the another one of the at least two segments and the second apex portion of the another one of the at least two segments, the first axial distance being equal to less than the second axial distance.

16. An endoscopic instrument according to claim 15, wherein a third axial distance is defined between the second apex portion of the one of the at least two segments and the first apex portion of the another one of the at least two segments and a fourth axial distance is defined between the first apex portion of the one of the at least two segments and the second apex portion of the one of the at least two segments, the third axial distance being less than or equal to the fourth axial distance.

17. An endoscopic instrument with a flexible shank, the flexible shank comprising:
two diametrically opposed joints; and
at least two segments connected to one another via the two diametrically opposed joints, wherein between axial face edges of the least two segments, the axial face edges facing one another, one of the axial face edges and another one of the axial face edges defining a gap, wherein an entire extension of the gap has an essentially constant width when the at least two segments are aligned with each other, wherein the gap extends in an angled manner at least once, each of the axial face edges comprising a first apex portion and a second apex portion, the first apex portion defining a greatest axial extent of a respective one of the least two segments, the second apex portion being located axially inward of the first apex portion with respect to a longitudinal axis of the respective one of the at least two segments, the first apex portion of one of the at least two segments being located axially opposite the second apex portion of another one of the at least two segments, the second apex portion of the one of the at least two segments being located axially opposite the first apex portion of the another one of the at least two segments, wherein a first axial distance is defined between the first apex portion of the one of the at least two segments and the second apex portion of the another one of the at least two segments and a second axial distance is defined between the first apex portion of the another one of the at least two segments and the second apex portion of the another one of the at least two segments, the first axial distance being equal to less than the second axial distance, the one of the axial face edges extending continuously from an area adjacent to one of the joints to an area adjacent to another one of the joints, the another one of the axial face edges extending continuously from another area adjacent to the one of the joints to another area adjacent to the another one of the joints, wherein each portion of an entire extension of the one of the axial face edges is located at a same distance from each portion of an entire extension of the another one of the axial face edges.

18. An endoscopic instrument according to claim 17, wherein a third axial distance is defined between the second apex portion of the one of the at least two segments and the first apex portion of the another one of the at least two segments and a fourth axial distance is defined between the first apex portion of the one of the at least two segments and the second apex portion of the one of the at least two segments, the third axial distance being less than or equal to the fourth axial distance.

* * * * *